(12) United States Patent
Carli et al.

(10) Patent No.: US 7,862,615 B2
(45) Date of Patent: Jan. 4, 2011

(54) INTERVERTEBRAL IMPLANT WITH TWO SHAPES

(75) Inventors: Olivier Carli, Guyancourt (FR); Pierre Bernard, Merignac (FR); Christian Mazel, Boulogne Billancourt (FR); David Ryan, Suresnes (FR)

(73) Assignee: Scient'x, Guyancourt (FR)

( * ) Notice: Subject to any disclaimer, the term of this patent is extended or adjusted under 35 U.S.C. 154(b) by 133 days.

(21) Appl. No.: 11/496,492

(22) Filed: Aug. 1, 2006

(65) Prior Publication Data

US 2007/0106298 A1 May 10, 2007

(30) Foreign Application Priority Data

Aug. 4, 2005 (FR) .................................. 05 08321

(51) Int. Cl.
*A61F 2/44* (2006.01)
(52) U.S. Cl. ..................................... 623/17.11; 606/249
(58) Field of Classification Search ... 623/17.11–17.16; 606/61, 246–249
See application file for complete search history.

(56) References Cited

U.S. PATENT DOCUMENTS

| 6,440,169 | B1 * | 8/2002 | Elberg et al. ............. 623/17.16 |
| 6,761,719 | B2 * | 7/2004 | Justis et al. .................... 606/61 |
| 2005/0055031 | A1 * | 3/2005 | Lim ............................. 606/99 |
| 2005/0261768 | A1 * | 11/2005 | Trieu ........................ 623/17.11 |
| 2006/0085070 | A1 * | 4/2006 | Kim ........................ 623/17.11 |
| 2006/0195102 | A1 * | 8/2006 | Malandain ................... 606/72 |

* cited by examiner

*Primary Examiner*—Thomas C Barrett
*Assistant Examiner*—Michael J Araj
(74) *Attorney, Agent, or Firm*—Michael R. Shevlin

(57) ABSTRACT

The invention concerns an intervertebral implant that includes a spacer designed firstly to assume an implantation shape in which the spacer has two opposed channels (3, 4) bordered by retaining wings (3a, 3b, 4a, 4b), intended to receive the two spinous processes of two vertebrae, and secondly an insertion shape in which the parts of the implant forming the channels (3, 4) are separated by a value (d), and on at least one of their sides are lacking the retaining wings (3a, 3b, 4a, 4b), characterized in that the implant (1) is made from a shape-memory material, so that the implant changes to its implantation shape when it is subjected to heat, and so that, in this implantation shape, the parts of the implant forming the channels (3, 4) are separated by a value (D) that is greater than the value(d) of the insertion shape, in order to ensure the separation of the spinous processes.

14 Claims, 2 Drawing Sheets

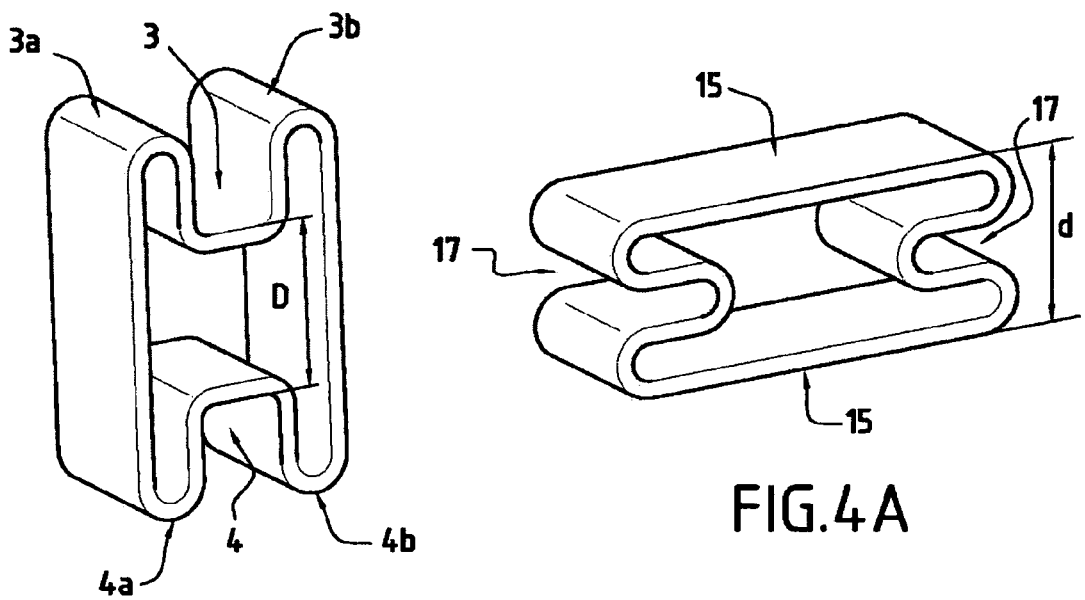
FIG.4
FIG.4A
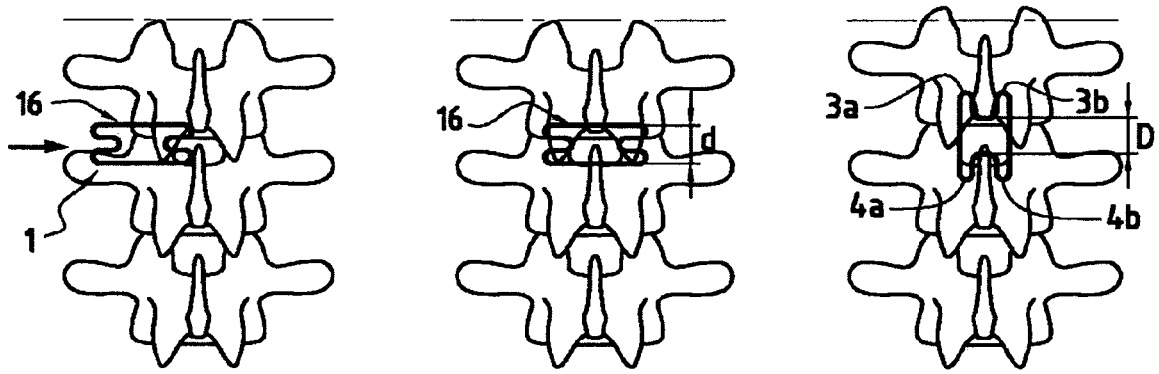
FIG.5A
FIG.5B
FIG.5C

INTERVERTEBRAL IMPLANT WITH TWO SHAPES

This present invention concerns the technical area of intervertebral implants designed to stabilise the vertebral column in the context of certain forces due to movements of the patient such as bending, stretching, twisting or lateral curvature.

The subject of the invention more precisely covers an intervertebral implant with a spacer intended to be inserted between the spinous processes which extend the rear part of the vertebrae in order to keep them apart. In a known manner, this spacer substitutes for the intervertebral disk when the latter is defective so as to limit the closeness of the rear part of the two vertebrae, which can lead to pain at the level of the vertebral column.

In previous designs, many spacer solutions have been proposed with a view to preventing contact between two vertebrae. For example, patent FR 2 799 640 described a spacer in which two opposing channels are created which are capable of accommodating the two spinous processes of two vertebrae. Each channel has two wings which are equipped with a link used to surround a portion of the surface of the process opposite to the bottom of the channel. The fitting of such a spacer requires perforation of the interspinal ligament of the overlying segment and the interspinal ligament of the underlying segment in order to stabilise the spacer.

From patent application WO 99/21500, we also know about an interspinal spacer that comes in a generally H shape and which is created in two parts. One of the parts includes a wing equipped with a stretching body intended to receive the other which has a wing. The fitting of this spacer requires resection of the interspinal ligament to allow lateral insertion of the spacer. However the assembly of the two parts requires a bilateral approach in relation to the spinous processes.

Document US 2005/055031 also described an ancillary for the introduction of an intervertebral implant made from a shape-memory material and having two opposed channels bordered by retaining wings. This ancillary has a clamp that is used to draw together the two retaining wings in order to allow the introduction of the implant. The removal of the clamp allows the wings to return to their initial positions. The introduction of the implant requires the use of an ancillary that imposes a large approach path.

The subject of the invention aims to remedy the drawbacks of the earlier technical solutions by proposing an interspinal spacer whose introduction can be effected by minimal surgery, meaning the least invasive possible.

In order to attain such an objective, the intervertebral implant includes a spacer that is designed firstly to assume an implantation shape in which the spacer has two opposed channels bordered by retaining wings intended to receive the two spinous processes of two vertebrae, and secondly an insertion shape in which the parts of the implant forming the channels are separated by a given value, and are lacking the retaining wings on at least one of their sides, characterised in that the implant is made from a shape-memory material so that the implant changes to its implantation shape when it is subjected to heat and that, in this implantation shape, the parts of the implant forming the channels are separated by a value greater than the value of the insertion shape, in order to effect the separation of the spinous processes.

According to one implementation characteristic, the intervertebral implant assumes its implantation shape when it is subjected to a temperature of at least 37° C.

According to another implementation characteristic, the intervertebral implant assumes its insertion shape when it is subjected to cold or to ambient temperature.

According to yet another implementation example, in its insertion shape, the implant is lacking the retaining wings on both of its sides.

According to this example, the implant in its insertion shape has an insertion part made of the parts forming the channels and the wings located on the two sides of the channels.

Advantageously, the insertion part has a rectangular profile.

According to one implementation variant, the insertion part assumes shapes of the spring type, in accordance with its height.

According to another implementation example, the implant, in its insertion shape, has an insertion part shaped by the parts forming the channels and the wings located on one of the sides of the channels.

According to one method of implementation of the invention, the implant is created in the form of a flexible ring.

According to this method of implementation, the ring is designed to have a centre part for each channel extended on each side by risers.

Advantageously, each riser bordering a channel is connected to the opposite riser bordering the other channel by means of a connecting branch.

Various other characteristics will emerge from the description provided below, with reference to the appended drawings which show, by way of non-limiting examples, forms of implementation of the subject of the invention.

FIGS. 4 and 4A are schematic views in perspective illustrating a third implementation example of an intervertebral implant shown respectively in an implantation shape and an insertion shape.

FIGS. 5A to 5C illustrate three characteristic stages of fitting the intervertebral implant illustrated in FIGS. 4 and 4A.

Figure 1:
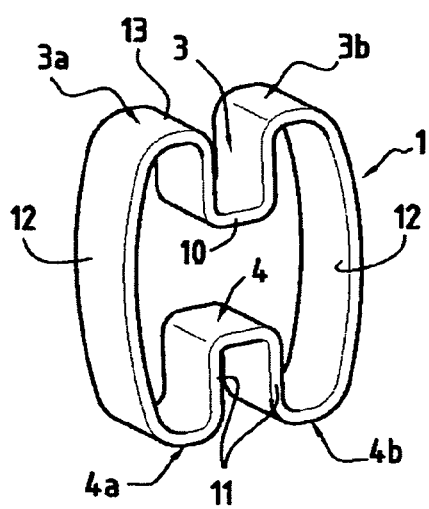
FIGS. 1 and 1A are views of a first implementation example of an intervertebral implant shown respectively in an implantation shape and an insertion shape.
Figure 3A:
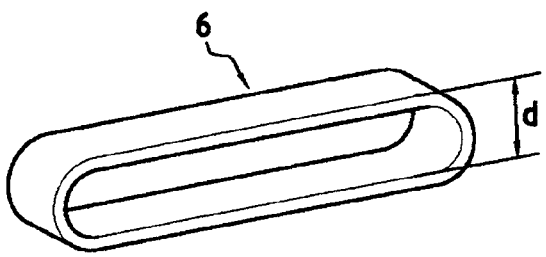
FIGS. 3A and 3B illustrate a second implementation example of an intervertebral implant shown respectively in its implantation shape and its insertion shape.
Figure 3B:
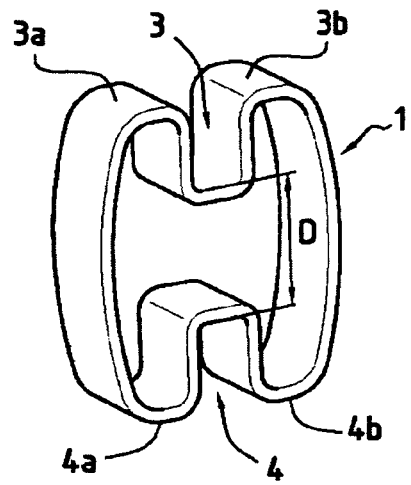

As can be seen from the drawings, the subject of the invention concerns an intervertebral implant 1 that has the form of a spacer. According to the invention, the implant 1 is made from a shape-memory material. For example, the implant 1 is made from a material of the Niti type, more commonly known as Nitinol. It should be understood that the implant 1 is intended to have at least two stable shapes, namely an insertion shape as illustrated in FIGS. 1A, 3A, and 4A, and an implantation shape as illustrated in FIGS. 1, 3B and 4.

It should be considered that in its implantation shape, the implant 1 is subjected to the heat of the patient, meaning that it is subjected to a temperature at least of the order of 37° C., or even higher. Thus, the implantation shape is determined during the creation of the implant and the material is programmed to deform reversibly in order to give it an insertion shape that is compatible with a unilateral surgical approach. Before it is fitted, and in order that it should assume its insertion shape, the implant is subjected to a lower temperature, that is to cooling in relation to the temperature that gives the implant its implantation shape. When the implant 1 is implanted, it is heated on contact with the body, and recovers its implantation shape. The implant 1 retains this implantation shape as long as it remains implanted in the body of the patient.

As can be seen more precisely in the implementation example illustrated in FIGS. 1, 1A, and 2A to 2C, in its implantation shape the implant 1 has (FIGS. 1 and 2C), two opposing channels 3 and 4 intended to accommodate the two spinous processes $E_1$, $E_2$ of two vertebrae. In the implantation shape of the implant, the channels 3, 4 are distant from each other by the value D of separation of the processes. Each channel 3, 4 is bordered on each side by a retaining wing 3a, 3b and 4a, 4b respectively.

Figure 1A:
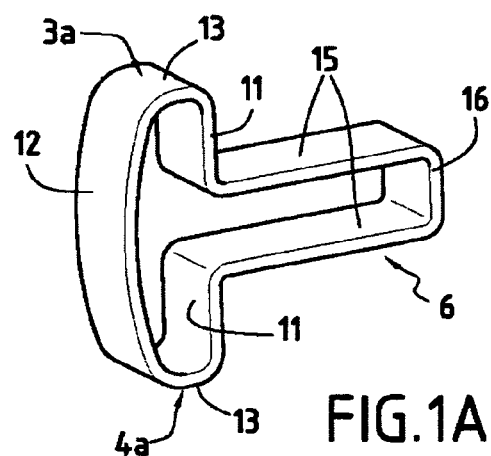
Figure 2A:
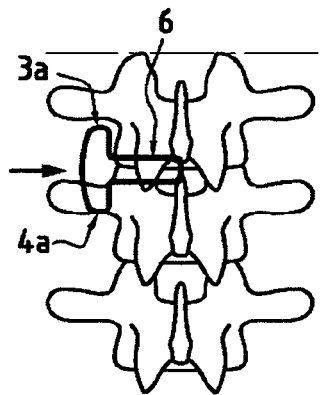
FIGS. 2A to 2C illustrate three typical stages of introduction of an intervertebral implant as illustrated in the FIGS. 1 and 1A.
Figure 2B:
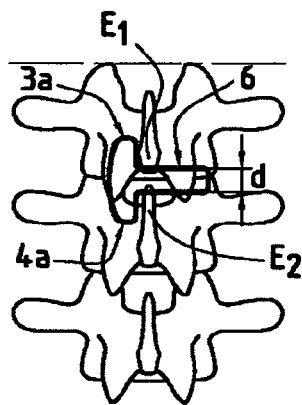
Figure 2C:
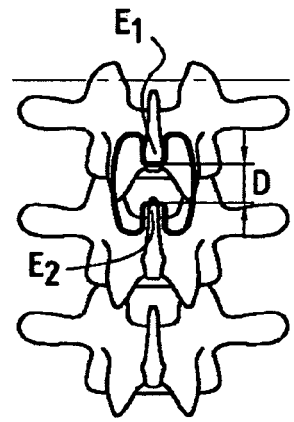

As illustrated more precisely in FIGS. 1A, 2A, and 2B, in its insertion shape, the implant 1 has an insertion part 6 whose height has a value d which is less than the separation value D assumed in the implantation shape. It should be considered that the insertion part 6 corresponds to the part of the implant intended to be engaged laterally, via a unique approach path, between the spinous processes. Up to a given width, this insertion part 6 has a height d at its free or rear end that allows lateral movement of the implant until it occupies its implantation position. In the example illustrated in FIG. 1A, this insertion part 6 corresponds to the parts forming the channels 3, 4 and the wings 3b, 4b located on the same side of channels 3 and 4. Thus in the example illustrated, in its insertion shape the implant 1 has the wings 3a, 4a extended by the insertion part 6.

The introduction of an implant 1 according to the invention follows directly from the above description. An incision of about 2 to 3 cm is made on the lateral edge of the spinous processes of the two vertebrae concerned. Where appropriate, this incision is made on the side where the surgeon has to create a decompression on a nerve root or on the spinal marrow. To this end, the surgeon effects muscular separation from the edge of the spinal process to the transverse processes. According to circumstances, this procedure is employed in order to reach the compressive herniated disc or the osteophytes which compress the dural sac. After effecting this medullar or radicular decompression, the implant is inserted via the same incision by perforating the interspinal ligament while preserving the superspinous ligament.

Prior to fitting the implant 1, it is taken to a temperature that causes it to assume its insertion shape. The implant 1 assumes its insertion shape when it is subjected to ambient temperature, typically between 20 and 25° C., or to cold for example, by contact cooling with an inert gas such as nitrogen. The implant is then inserted by the translation of its insertion part 6 (FIG. 2A) into the intervertebral space until the wings 3a, 4a are practically at the level of the processes $E_1$ and $E_2$ (FIG. 2B). On making contact with the body, the implant 1 is subjected to heating so that it recovers its initial shape, called the implantation shape. Note that the heating of the implant 1 can also be effected from an external source such as sterile warm water, at a temperature of between 30 and 50° C. for example.

During the return of the implant to its definitive implantation shape (FIG. 2C), the distance between the vertebrae $E_1$, $E_2$ progresses from the value d to the value D. The parts of the implant forming the channels 3, 4 are separated, in the implantation shape, by a value D which is greater than the value of the insertion shape, in order to ensure the separation of the spinous processes. This separation of the spinous processes has the effect of relieving the articulations and the rear part of the intervertebral disk. Naturally, the value of the separation D is adapted to the capacity of the vertebral column to accept this separation, and varies according to the stage concerned and the amplitude of separation wanted (from 3 to 5 mm for example). It should be understood that the implant 1 made from a shape-memory material is designed, when it is subjected to heat, to pass from an insertion shape to an implantation shape in order to effect the separation of the spinous processes.

According to one advantageous implementation characteristic, as illustrated in FIGS. 1 and 1A, the implant 1 is created in the form of a flexible ring. In the example illustrated, the ring is closed. Naturally, an open ring can also be envisaged.

According to this implementation example, in the implantation shape, the ring is designed to have, for each channel 3, 4, a centre part 10 that is extended on each side more or less at right angles by risers 11. The risers 11 located on a given side of the channels 3, 4 are connected together to a connecting branch 12 by means of connecting parts 13. Each connecting part 13 has a rounded contour oriented away from the neighbouring channel. The connecting branch 12 can also have a slightly curved profile. In general, such a ring has no sharp corners.

In its insertion shape, the ring has the insertion part 6 formed by two flat faces 15 parallel to each other and connected together by a connection zone 16 which is preferably rounded. Opposite to the connection zone 16, the two flat faces 15 are extended more or less at right angles by risers 11 which are connected together by a connecting branch 12 by means of connecting parts 13 so as to constitute retaining wings 3a, 4a.

Referring to FIGS. 1 and 1A, the ring shaped spacer of the implant 1 has an anterior-posterior dimension that is both (i) transverse to the axis of the spinous processes (FIG. 2A) (as well as transverse to heights (d) and (D)), and (ii) transverse to an insertion direction of the implant (see arrow, FIG. 2A). It is further apparent from FIGS. 1 and 1A, that when the implant 1 changes from the insertion shape (FIG. 1A) to the implantation shape (FIG. 1), the anterior-posterior dimension of the ring shape spacer does not change; i.e., it is the same for both the insertion and implantation shapes.

FIGS. 3A and 3B illustrate another implementation example of an intervertebral implant 1 whose insertion shape is different from the insertion shape illustrated in FIG. 1A. The implantation shape of the implant 1 illustrated in FIG. 3B is more or less the same as the implantation shape of the implant 1 illustrated in FIG. 1. According to this implementation example, in its insertion shape, the implant has a constant height which is a rectangular profile. In other words, the implant 1 includes an insertion part 6 of height d which extends over the full width of the implant 1. Thus, in its insertion shape, the implant 1 has neither wings 3a and 4a nor wings 3b and 4b.

FIGS. 4 and 4A illustrate another implementation variant in which the implant 1 has an insertion shape of different form. In its insertion shape, illustrated in FIG. 4A, the implant 1 includes an insertion part 6 that has a constant height d over all of its width. The insertion part 6 is formed by two flat faces 15. In the insertion position 6, the two flat faces 15 are connected together and to each other at their ends, by shapes 17 such as the omega-shaped folds in the example illustrated (FIG. 5A, 5B). Such spring-like shapes 17 in contribute to form the wings 3a, 3b, 4a, 4b of the implant when the latter assumes its implantation shape as illustrated in FIGS. 4 and 5C.

Note that whatever the method of implementation described above, the implant 1 always has a damping property that comes from the flexibility of the ring, which is capable of supporting the load variations concerned.

The invention is not limited to the examples described and illustrated, since various modifications can be made to it without moving outside of its scope.

The invention claimed is:

1. An intervertebral implant that changes configuration between an insertion shape and an implantation shape, wherein,
in the implantation shape, the implant includes a spacer having two opposed channels bordered by retaining wings, the channels intended to receive two spinous processes of two vertebrae, parts of the spacer forming the opposed channels are separated by a value (D) that ensures the separation of the spinous processes, and
in the insertion shape, parts of the implant forming the opposed channels are separated by a value (d) which is less than the value (D) and which allows the spacer to be inserted between the spinous processes, the spacer in the insertion shape is deprived of a retaining wing on at least one of its sides,
wherein the value corresponding to an anterior-posterior dimension of the spacer which is both (i) transverse to the axis of the two spinous processes and (ii) transverse to an insertion direction of the implant is the same for the insertion and implantation shapes,
the spacer being made entirely from a shape-memory material so that the spacer is in the insertion shape at a first temperature and automatically changes from the insertion shape to the implantation shape when subjected to a second relatively higher temperature.

2. An intervertebral implant according to claim 1, wherein, in its insertion shape, the spacer is lacking the retaining wings on its two sides.

3. An intervertebral implant according to claim 2, wherein, in its insertion shape, the spacer has an insertion part formed by the parts forming the channels and the wings located on the two sides of the channels.

4. An intervertebral implant according to claim 3, wherein the insertion part has a rectangular profile.

5. An intervertebral implant according to claim 3, wherein, according to its height, the insertion part has shapes of a spring type.

6. An intervertebral implant according to claim 1, wherein, in its insertion shape, the spacer has an insertion part formed by the parts forming the channels and the wings located on one of the sides of the channels.

7. An intervertebral implant according to claim 1, wherein the implant is created in the form of a flexible ring.

8. An intervertebral implant according to claim 7, wherein, for each channel, the ring is designed to have a center part extended on each side by risers.

9. An intervertebral implant according to claim 8, wherein each riser bordering a channel is connected to the opposite riser bordering the other channel by means of a connecting branch.

10. An intervertebral implant according to claim 1, wherein the first temperature is ambient temperature.

11. An intervertebral implant according to claim 1, wherein the first temperature is between 20° and 25° C.

12. An intervertebral implant according to claim 1, wherein the first temperature is colder than 20° C.

13. An intervertebral implant according to claim 1, wherein the second temperature is between 30° C. and 50° C.

14. An intervertebral implant according to claim 1, wherein the second temperature is at least 37° C.

* * * * *